(12) United States Patent
Kamrava

(10) Patent No.: US 12,741,099 B2
(45) Date of Patent: Sep. 22, 2026

(54) DISCRETE DOSE CONTROL AND OVERDOSE PREVENTION MECHANISM

(71) Applicant: Becton, Dickinson and Company, Franklin Lakes, NJ (US)

(72) Inventor: Soroush Kamrava, Everett, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 490 days.

(21) Appl. No.: 18/259,605

(22) PCT Filed: Dec. 28, 2021

(86) PCT No.: PCT/US2021/065407
§ 371 (c)(1),
(2) Date: Jun. 28, 2023

(87) PCT Pub. No.: WO2022/147053
PCT Pub. Date: Jul. 7, 2022

(65) Prior Publication Data

US 2024/0058546 A1 Feb. 22, 2024

Related U.S. Application Data

(60) Provisional application No. 63/133,771, filed on Jan. 4, 2021.

(51) Int. Cl.
*A61M 5/315* (2006.01)

(52) U.S. Cl.
CPC ............................... *A61M 5/31573* (2013.01)

(58) Field of Classification Search
CPC .......... A61M 5/31573; A61M 5/31575; A61M 5/31565; A61M 5/315; A61M 5/31;
(Continued)

(56) References Cited

U.S. PATENT DOCUMENTS 6,551,277 B1 4/2003 Ford
2016/0317741 A1 11/2016 List
(Continued)

FOREIGN PATENT DOCUMENTS

CA 3 074 354 A1 3/2019
CN 1302213 A 7/2001
(Continued)

OTHER PUBLICATIONS

International Search Report dated Apr. 29, 2022, which issued in the corresponding PCT Patent Application No. PCT/US2021/065407.

*Primary Examiner* — Kevin C Sirmons
*Assistant Examiner* — Alexandra Lalonde
(74) *Attorney, Agent, or Firm* — Dickinson Wright PLLC

(57) ABSTRACT

A dose control and overrun protection mechanism is provided for use in fluid delivery devices such as wearable infusion pumps and medication delivery pens. The mechanism comprises oppositely rotating spur gears with surface features that guide a pin on a plate rotating along a desired arc path (e.g., less than 180 degrees) in alternating directions per a delivery cycle of a predetermined dose amount. The surface features are configured to controllably rotate one of the spur gears and output a selected amount of rotation to another component in a power train of a fluid delivery device regardless of a direction of an input of an actuator and regardless of whether the actuator rotates beyond the desired arc path.

12 Claims, 16 Drawing Sheets

(58) Field of Classification Search
CPC .............. A61M 5/178; A61M 5/14248; A61M 5/14244; A61M 5/142; A61M 5/14; A61M 5/1413; A61M 5/31511; A61M 5/31556; A61M 5/3155; A61M 5/31525; A61M 5/31526; A61M 5/3153; A61M 5/31533; A61M 5/31535; A61M 5/31545; A61M 5/31548; A61M 5/31558; A61M 5/31551; A61M 5/31553; A61M 5/31555; A61M 2039/226; A61M 2005/3152; A61M 2005/3154
See application file for complete search history.

(56) References Cited

U.S. PATENT DOCUMENTS

| | | | | |
|---|---|---|---|---|
| 2018/0055995 | A1 | 3/2018 | Hanson et al. | |
| 2021/0128830 | A1* | 5/2021 | Hanson .............. | A61M 5/1454 |

FOREIGN PATENT DOCUMENTS

| | | | |
|---|---|---|---|
| CN | 105102021 | A | 11/2015 |
| CN | 107810020 | A | 3/2018 |
| CN | 217430582 | U | 9/2022 |
| EP | 3 545 988 | A1 | 10/2019 |
| WO | WO2016145094 | A2 | 9/2016 |

* cited by examiner 10
19
12
14
16
20
22
18

DISCRETE DOSE CONTROL AND OVERDOSE PREVENTION MECHANISM

BACKGROUND

Field

The present disclosure and technical solution described herein generally relate to dose control and overdose prevention in fluid delivery devices used for medication delivery, and more particularly to a mechanism for converting input energy from an actuator to output energy to the next component in the powertrain of the fluid delivery device in a manner that controls fluid delivery device to deliver only a single dose per cycle and stops energy transfer to the powertrain when the actuator rotates beyond desired operation point.

Description of Related Art

Overdose is the application of a drug in quantities greater than intended dose and may result in intolerable risks to users. Overdose in drug delivery devices may happen because of a malfunction of any of the components responsible for dose delivery. Namely, these components are generally an actuator, electronics, and software. A need exists for overdose prevention in fluid delivery devices used for medication delivery.

SUMMARY

Problems such as overdose are overcome, and additional advantages are realized, by illustrative embodiments described herein.

In a fluid delivery device with a drive mechanism that uses a rotary input to control fluid delivery components and an actuator to operate the drive mechanism, an overrun prevention mechanism is provided having first and second spur gears comprising gear teeth and disposed adjacent to each other to engage a selected number of their corresponding gear teeth, the first spur gear being rotatable clockwise and the second spur gear rotatable counterclockwise, and a plate with pin actuated by the actuator in the fluid delivery device to rotate a controlled amount during a cycle to move the pin in an arc path relative to the first and second spur gears. The plate is actuated to rotate in clockwise and counterclockwise directions in alternating cycles. The first and second spur gears each have a face directed toward the plate with pin. Each face is configured with at least one surface feature along which the pin can follow as the plate is rotating. The surface feature of each of the spur gears is contacted by the pin when traveling toward respective ends of the arc path to rotate that spur gear by a selected amount and teeth of that spur gear engaging teeth of the other spur gear to impart rotation. The surface feature of each of the spur gears is also configured to lose contact with the pin at the respective end of the arc path before the actuator reverses direction of rotation of the plate to commence another cycle.

In accordance with an aspect of illustrative embodiments, an input to the overrun prevention mechanism corresponds to 126 degrees of rotation of the plate along the arc path during a cycle, and the spur gears are configured to rotate 90 degrees during that cycle. For example, an output of the overrun prevention mechanism is a 90 degree rotation imparted by one of the spur gears being rotated 90 degrees during a cycle. As a further example, the fluid delivery device has gear train components configured to receive the output of the overrun prevention mechanism as an input and to generate a second output of smaller rotation for application to the drive mechanism to achieve a fluid dose of predetermined amount. In addition, by way of another example, the fluid delivery device can be a syringe-type pump that moves a plunger in a barrel-type reservoir and the drive mechanism comprises telescopic nested screws operable to move the plunger, and the second output is provided to the drive mechanism to move the plunger a distance commensurate to deliver the fluid dose of predetermined amount.

In accordance with an aspect of illustrative embodiments, the at least one surface feature comprises two arcuate grooves that define two double convex lens-shaped protrusions disposed on either side of a center double concave lens-shaped protrusion. For example, a convex surface on the double concave lens-shaped protrusion is contacted by the pin when traveling toward respective an end of the arc path to rotate that spur gear by a selected amount. As another example, the two double convex lens-shaped protrusions and the center double concave lens-shaped protrusion are configured to lose engagement of the pin to not rotate further once the pin has reached the end of the arc path.

In accordance with an aspect of illustrative embodiments, the at least one surface feature comprises half-teardrop-shaped protrusions, each having a flat surface and a convex surface. For example, half-teardrop-shaped protrusions are arranged diagonally opposite each other on the face of each of the spur gears with their respective flat surfaces facing each other.

In accordance with an aspect of illustrative embodiments, the overrun prevention mechanism is provided with a sensor for detecting when the pin reaches an end of the arc path. For example, the fluid delivery device is configured to have a processor to receive outputs of the sensor and to control the actuator to reverse direction when the outputs indicate an end of the arc path has been reached by the pin.

Additional and/or other aspects and advantages of illustrative embodiments will be set forth in the description that follows, or will be apparent from the description, or may be learned by practice of the illustrative embodiments. The illustrative embodiments may comprise apparatuses and methods for operating same having one or more of the above aspects, and/or one or more of the features and combinations thereof. The illustrative embodiments may comprise one or more of the features and/or combinations of the above aspects as recited, for example, in the attached claims

BRIEF DESCRIPTION OF THE DRAWINGS

The above and/or other aspects and advantages of the illustrative embodiments will be more readily appreciated from the following detailed description, taken in conjunction with the accompanying drawings, of which.

Throughout the drawing figures, like reference numbers will be understood to refer to like elements, features and structures.

DETAILED DESCRIPTION OF ILLUSTRATIVE EMBODIMENTS

Figure 1:
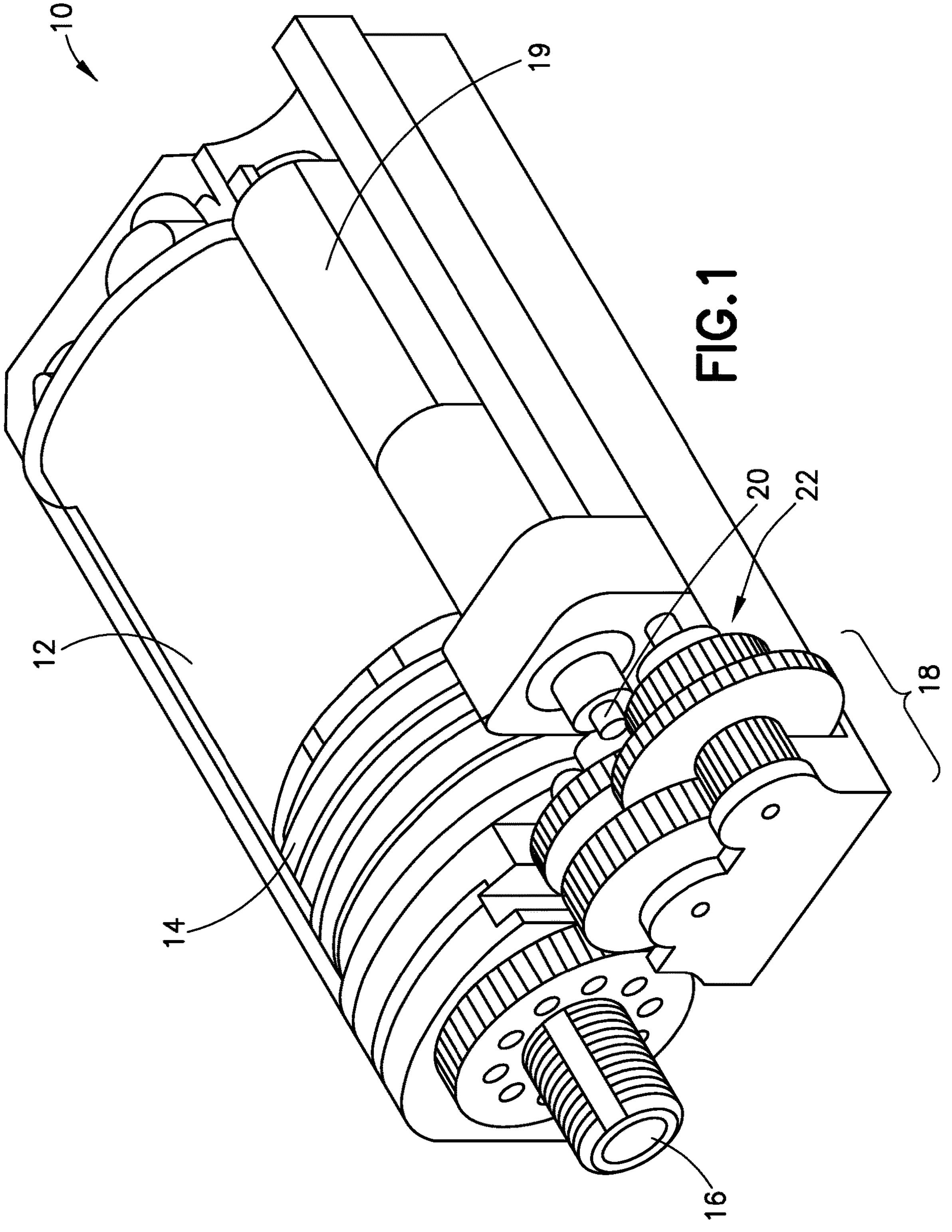
FIG. 1 is a perspective top view of an example fluid delivery device with the top and baseplate removed for clarity.

Reference will now be made in detail to illustrative embodiments, which are depicted in the accompanying drawings. The embodiments described herein exemplify, but do not limit, the illustrative embodiments by referring to the drawings.

User risk involved with overdose can be reduced by using various design solutions. These solutions could in nature be mechanical, electrical, algorithmic or a combination of any of them. One mechanical solution is a Geneva mechanism or Geneva drive, which is a mechanical mechanism that converts continuous input motion to a discrete output motion using a drive wheel with pin and driven wheel with slots. As the drive wheel rotates, the pin enters a slot in the driven well, thereby turning the driven wheel until it is rotated enough for the pin to leave the slot as it continues to travel with rotating drive wheel. The degree of turn of the driven wheel depends on the number of slots in the driven wheel, among other factors. The Geneva mechanism, however, does not have the ability to stop the output motion in case of overrunning input.

A technical solution described herein provides a novel mechanical solution for dose control and overdose prevention in drug delivery devices such as a wearable infusion device or drug delivery pen used for insulin delivery, for example. The technical solution is an overrun prevention mechanism provided in the powertrain of a fluid delivery device. The powertrain can comprise, for example, a gear train situated between an actuator and a drive mechanism for a plunger in a fluid reservoir of the fluid delivery device. The overrun prevention mechanism described herein in accordance with the technical solution and example embodiments receives input power (e.g., torque×speed) directly or indirectly from an actuator (e.g., a motor) and delivers an output power (e.g., torque×speed) to the next component in the powertrain. The overrun prevention mechanism is designed to regulate motion by physically saturating the mechanism's output such that its output and corresponding output of any connected intermediate power train components are commensurate to the desired dose, and yet also stopping the energy transfer when the actuator rotates beyond a desired operation point.

The overrun prevention mechanism is a discrete operating mechanism and delivers only one dose in each cycle. A cycle is understood to be a designated amount of movement of the actuator and overrun prevention mechanism to control the drive mechanism, and any intervening powertrain components, in the fluid delivery device to deliver a predetermined quantity of fluid from the fluid reservoir. For example, as described below, a cycle can be a reversible partial rotation of the actuator input shaft to achieve travel of a overrun prevention mechanism component with a pin or cam follower along an arcuate path of less than 180 degrees (e.g., 126 degrees) to achieve an output rotation of 90 degrees that is imparted to intermediate powertrain components to reduce their output to a smaller input for the drive mechanism to achieve the desired dosing of a predetermined quantity of fluid. In accordance with aspects of the technical solution and example embodiments of the overrun prevention mechanism, the actuator needs to stop and rotate in the reverse direction to initiate another dose delivery cycle. Regardless of the input rotational direction of the actuator, the output of overrun prevention mechanism rotates in a single direction. Reversal of the input rotational direction is needed to progress into next delivery cycle until the desired dose amount is dispensed.

The overrun prevention mechanism operates based on the physical interaction between one or more dowel pins in a plate, and the cam surface features on two spur gears. The way that load transfers between these components are highly dependent to the geometry of them, and the input torque profile can be tuned by changing the geometry of these features, which are described below in connection with two example embodiments illustrated in FIGS. 4A-4F and FIGS. 5A-5G, respectively. For illustrative purposes, the example embodiments are described in connection with an example fluid delivery device such as a wearable infusion device as shown in FIG. 1 having a syringe-type pump.

With reference to FIG. 1, an example fluid delivery device 10 is shown without a cover and base plate for clarity. The fluid delivery device 10 has a syringe barrel-type reservoir 12 with a plunger 14 that can be controlled by a drive mechanism 16 to extend into the reservoir 12 a desired amount to expel a desired amount of fluid therefrom. The drive mechanism can be, for example, an arrangement of telescopic nested screws that have an innermost screw connected to the plunger and that are controllably extended by a powertrain. For example, the powertrain can comprise a rotational actuator (e.g., a motor) 19 with input shaft 20 connected to a gear train 18 with respective gears that are, in turn, be connected to the drive mechanism 16. Example embodiments of the overrun prevention mechanism 22 illustrate the mechanism 22 to be located near the actuator with intermediate gears arranged between the mechanism 22 and the drive mechanism 16. It is to be understood, however, that the overrun prevention mechanism 22 can be connected at any point along the powertrain between the actuator 19 and drive mechanism 16. Further, it is to be understood that the actuator can be other types of actuators besides a motor that are capable to providing at least half-revolution and reversible rotational input (e.g., hydraulic, spring-loaded, hand-powered, and solenoid actuators), and the drive mechanism 16 need not be limited to telescopic nested screws for driving a plunger in a barrel reservoir. For example, the overrun prevention mechanism 22 can be employed in the powertrains of various types of positive displacement pumps.

In these example embodiments, 126 degrees of rotation in the input results in 90° rotation in the output by the overrun prevention mechanism, which can be reduced, for example, to 2.57 degree level of input at the pump level (e.g., input to a drive mechanism 16 having telescope nested screws) using a set of intermediate spur gears 18. The 2.57 degree rotation at the pump (e.g., syringe-type pump with barrel and plunger) is equivalent to one dose delivery. As described below, the overrun prevention mechanism is designed in a way that rotating the input for more than 126 degrees does not change the 90 degree rotation in output. Hence, actuating the input shaft and connected plate with pin slightly more than 126 degrees guarantees the accuracy of the dosing. Also, an electrical switch can be added to the fluid deliver device control system to sense the 126 degree input rotation and send a stop and reverse command to the actuator. It is to be understood that different degrees of rotation for the input and output of the overrun prevention mechanism 22 can be tuned, depending on the desired dose delivery amount and design features of the drive mechanism 16 and other components of the fluid delivery device 10.

Figure 2:
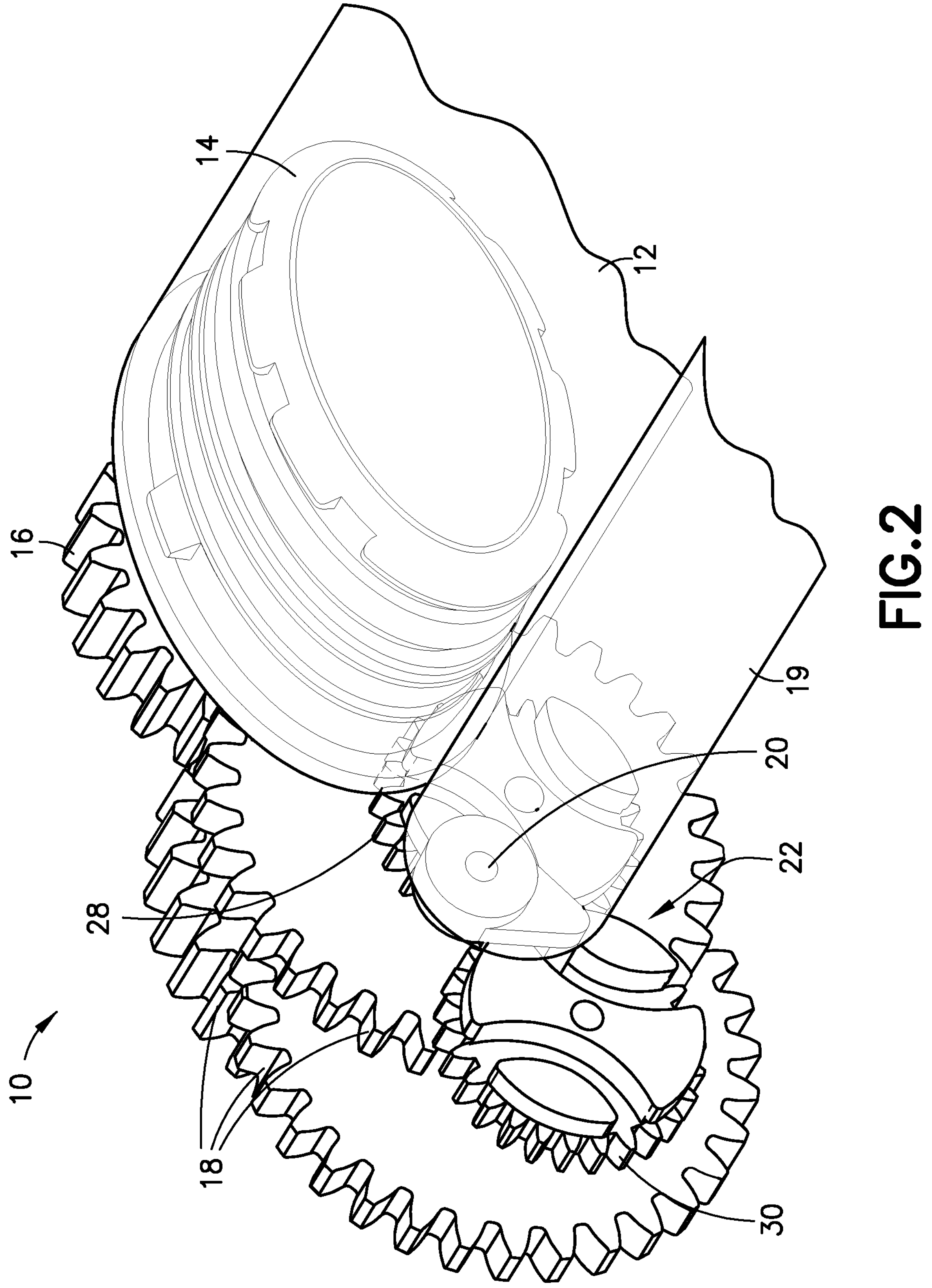
FIG. 2 is a side perspective view of a portion of an actuator, gear train and drive mechanism for a plunger in the syringe-barrel type reservoir of the device in FIG. 1.

With reference to FIG. 2, the overrun prevention mechanism 22 generally comprises two spur gears 28 and 30 and a plate 24 or other member provided with one or more pins 26. The pin(s) 26 cooperate with features on the front faces of the spur gears 28 and 30 as described below to ensure the pin completes a desired actuate path 32 yet only delivers a predetermined output (e.g., 90 degree rotation of the spur gears 28 and 30) to maintain consistently complete doses. Even if the actuator 19 or other component malfunctions and causes an overrun, the overrun prevention mechanism 22 components are configured to prevent more than an output commensurate to delivering a predetermined dose amount for that cycle.

Figure 3A:
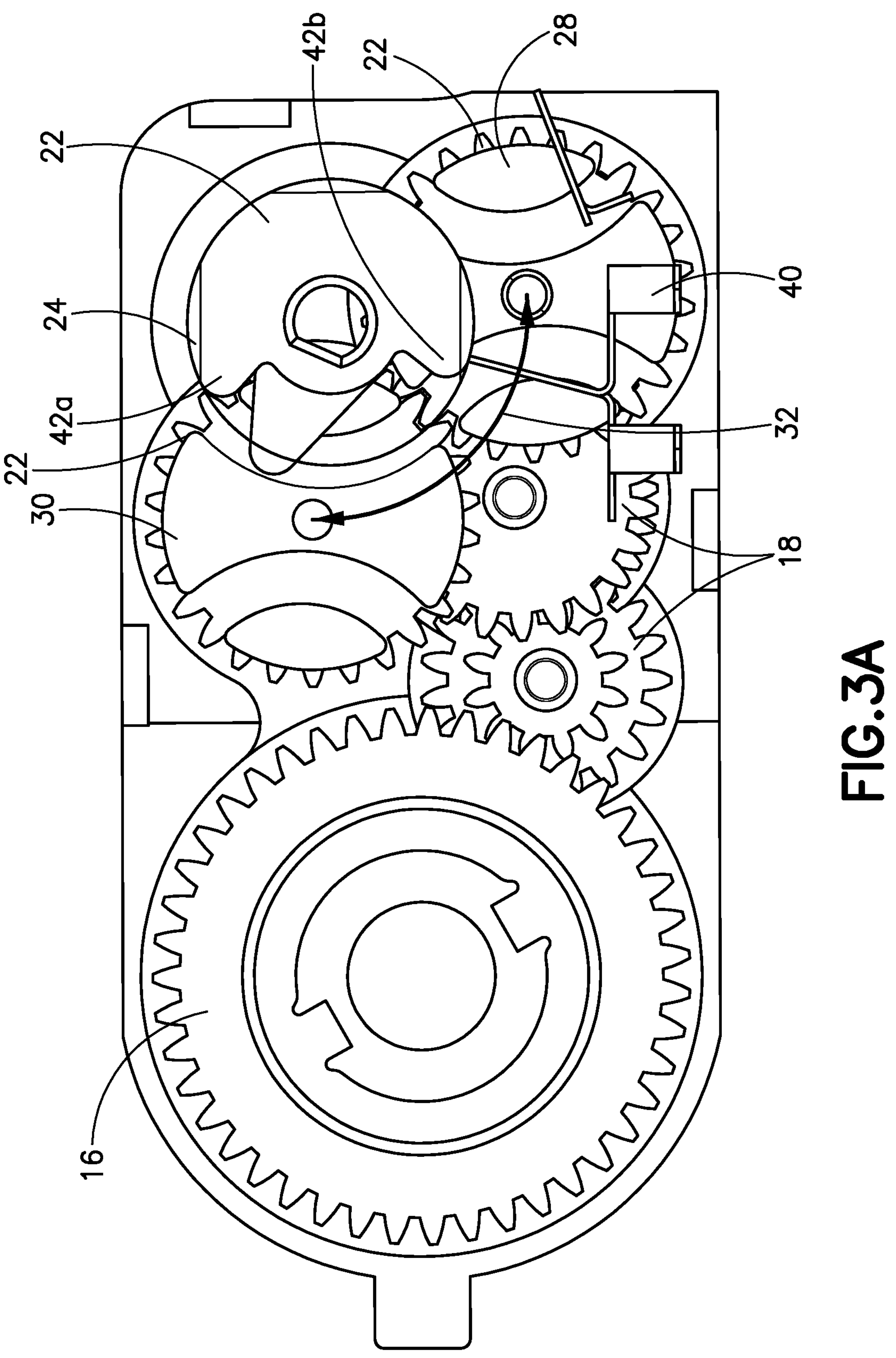
FIGS. 3A and 3B are side views of a gear train and drive mechanism for an example fluid delivery device with example end stop circuit.
Figure 3B:
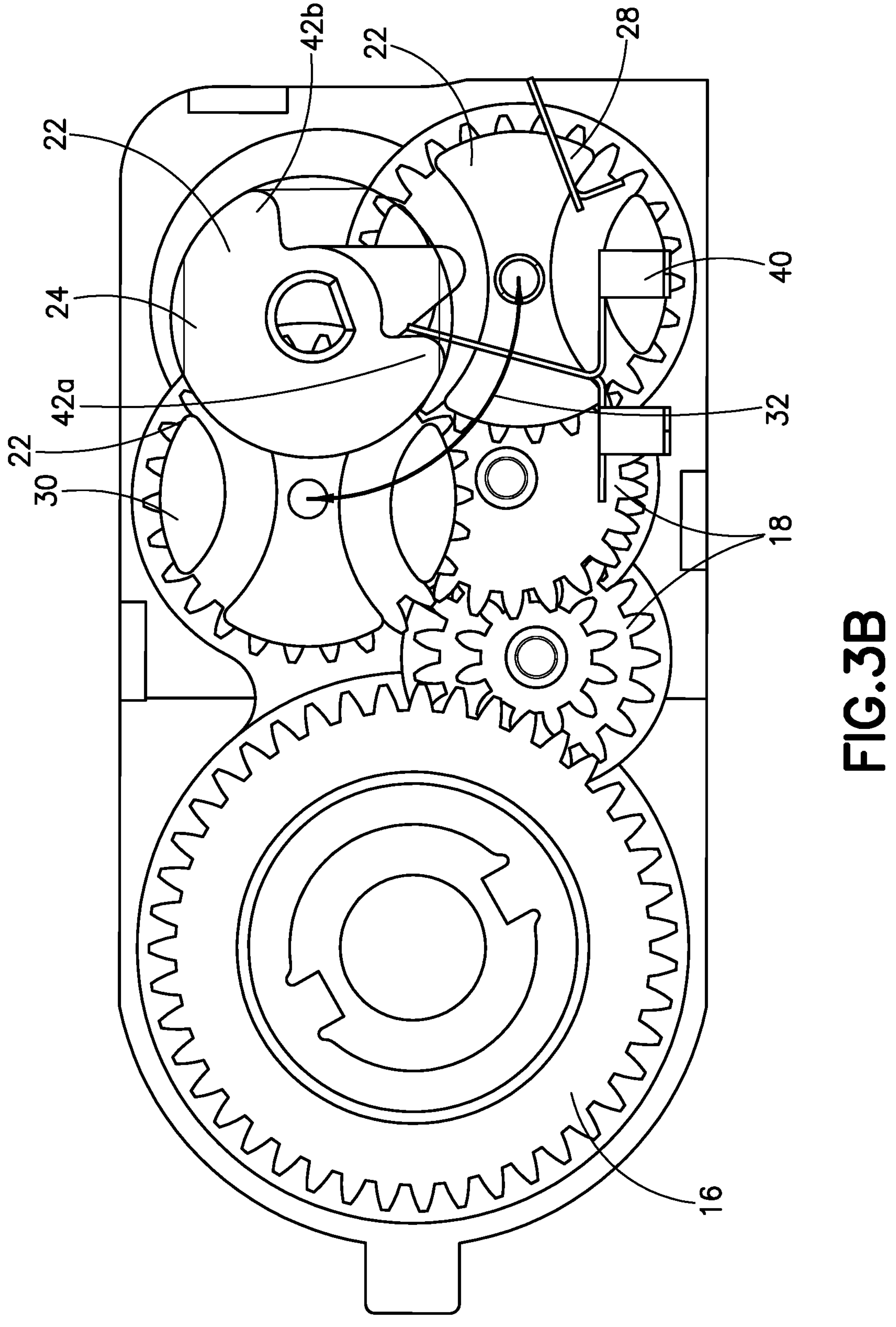

With reference to FIGS. 3A and 3B, the overrun prevention mechanism 22 components are assembled in a different configuration that is more vertical relative to gear train components 18 than as shown in FIG. 2 and the example embodiments described below. The configuration shown in FIGS. 3A and 3B can help to save space in the fluid delivery device 10 and minimize its dimensions. Also shown in FIGS. 3A and 3B is an example detection circuit 40 for when the direction of the actuator 19 should be reversed. For example, a plate 24 with pin 26 can be configured as electrically conductive and can short a circuit 40 when either of its end stop positions 42*a,b* reaches the circuit 40 at the end of an arc 32, thereby generating a signal for a controller to detect and command stopping and reversing direction by the actuator 19. Other methods of end of arc 32 detection, however, can be used.

An example embodiment of overrun prevention mechanism 22 will now be described with reference to FIGS. 4A through 4F. The front face 36 of each of the spur gears 28, 30 has two arcuate grooves or traces 50 that define two double convex lens-shaped protrusions 52 and a center double concave lens-shaped protrusion 54. These features 50, 52 and 54 on the faces 36 of the spur gears 28, 30 cooperate to intermittently provide an S-shaped path 34 for the pin 26 and cam surfaces with which to prevent further travel of the pin along an arc 32.

Spur gear 30 rotates counterclockwise (CCW) regardless of input direction of actuator input shaft 20. Spur gear 28 rotates clockwise (CW) regardless of input direction of actuator input shaft 20. The actuator input shaft 20 is rotated alternately CW and CCW to allow the pin 26 to travel through an arc 32 (e.g., 126 degrees or some other value less than 180 degrees) before stopping and reversing and traveling the arc in the opposite direction. The plate 24 with pin 26 in FIGS. 4A-4F is shown without the connected input shaft 20 for clarity.

Figure 4A:
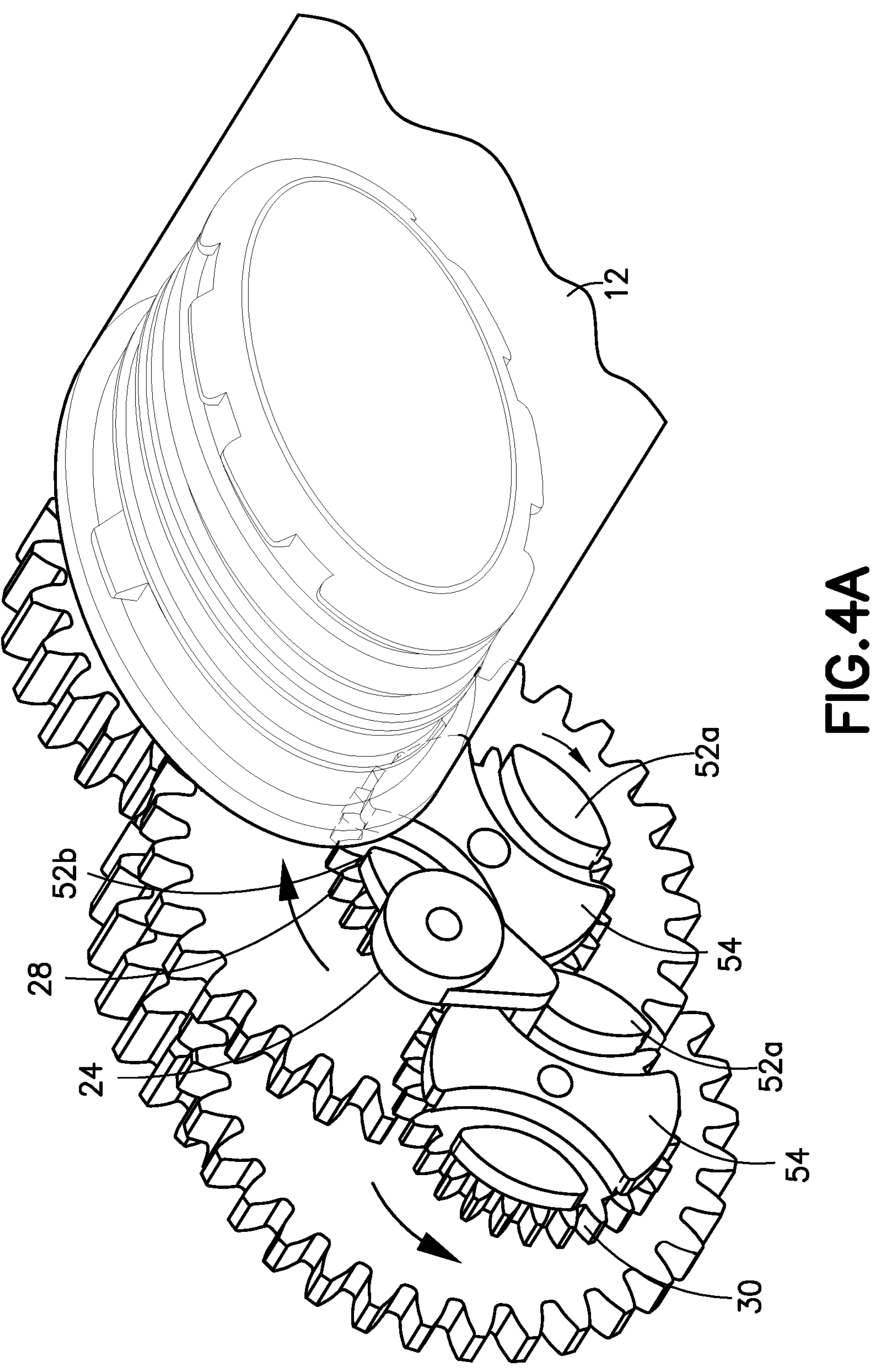
FIGS. 4A, 4B, 4C, 4D, 4E and 4F are side views of an actuator and gear train constructed in accordance with an illustrative embodiment for operating a drive mechanism of the example fluid delivery device of FIG. 1.
Figure 4B:
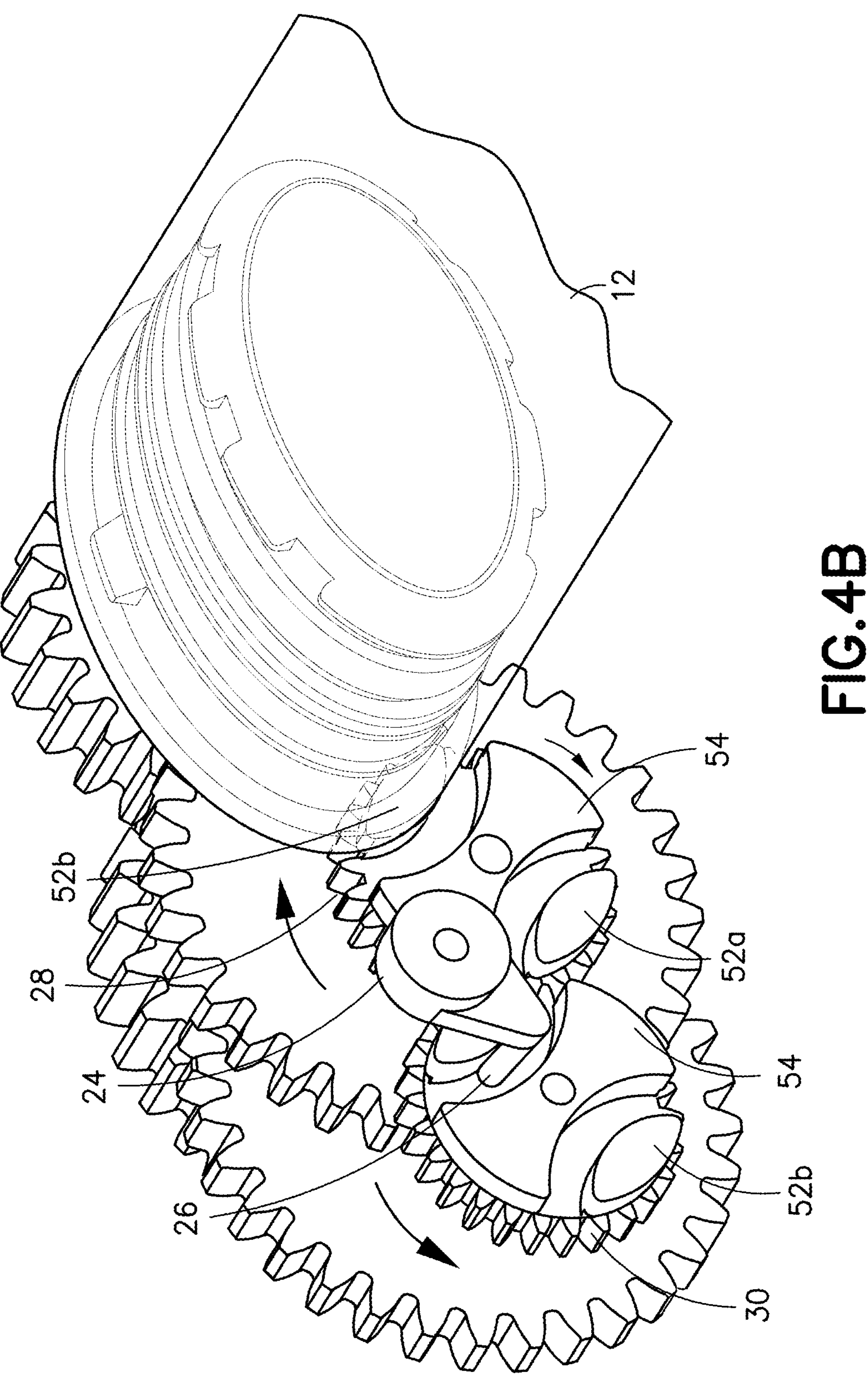
Figure 4C:
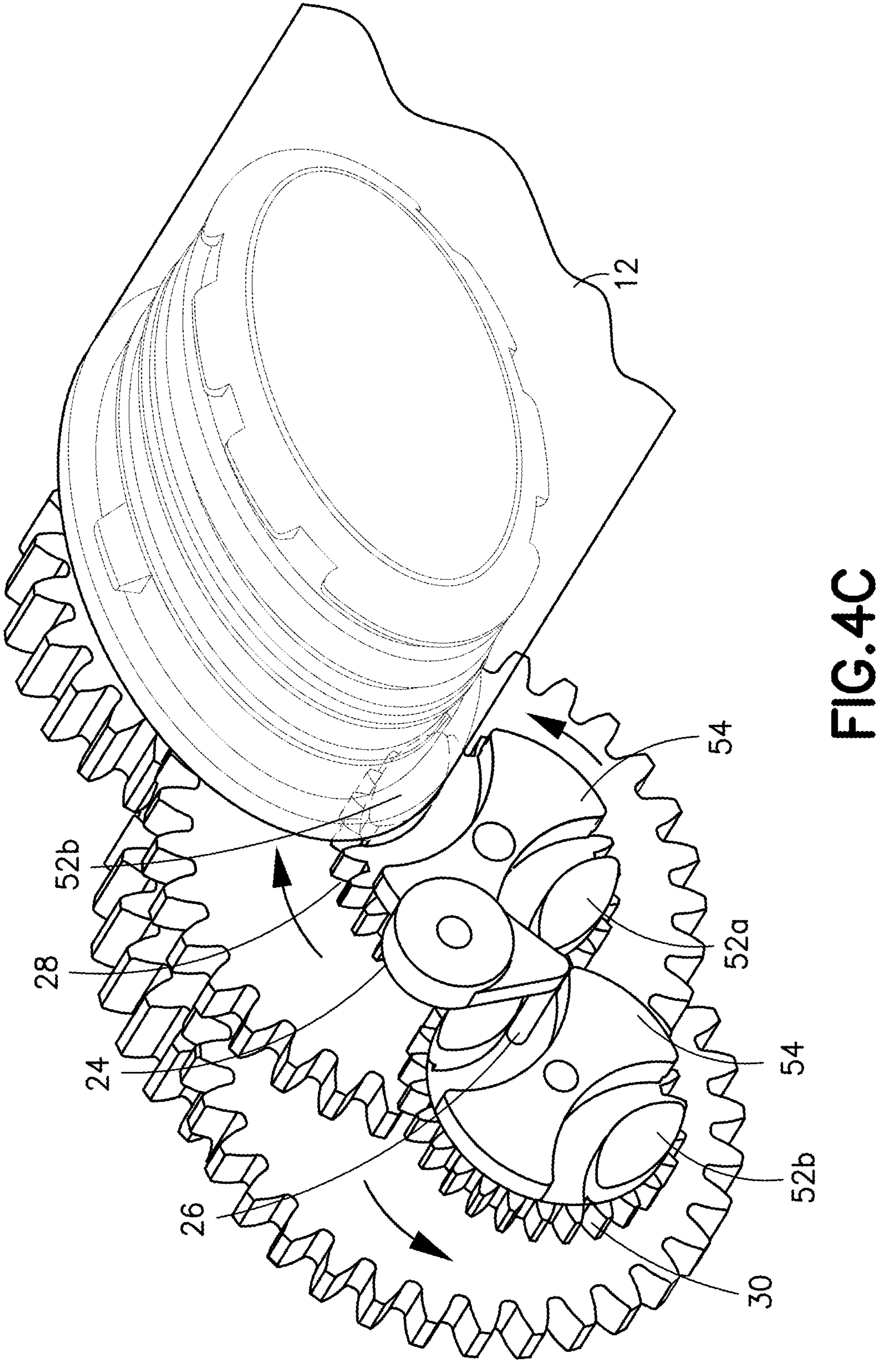

FIG. 4A shows the plate 24 with pin 26 rotating CW from a bottom arc position. As the input shaft connected to the plate 24 continues to turn the plate CW, the pin 26 follows the lower concave surface of the concave lens-shaped protrusion 54 on spur gear 30 shown in FIG. 4A and moves the spur gear CCW 90 degrees as shown in FIG. 4B. The cooperating teeth on the spur gears 28 and 30 causes the spur gear 28 to rotate CW 90 degrees. The cam surfaces of the double convex lens-shaped protrusion 52*a* and the double concave lens-shaped protrusion 54 on the spur gear 30 are configured to no longer push the pin 26 once it reaches a top end of the arc 32. Another S-shaped path 34 is established by respective grooves 50 on the spur gears 28, 30 for the CCW movement of the pin 26 along the arc 32 as shown in FIG. 4C after the actuator 19 stops and reverses direction of the input shaft 20 connected to the plate 34.

Figure 4D:
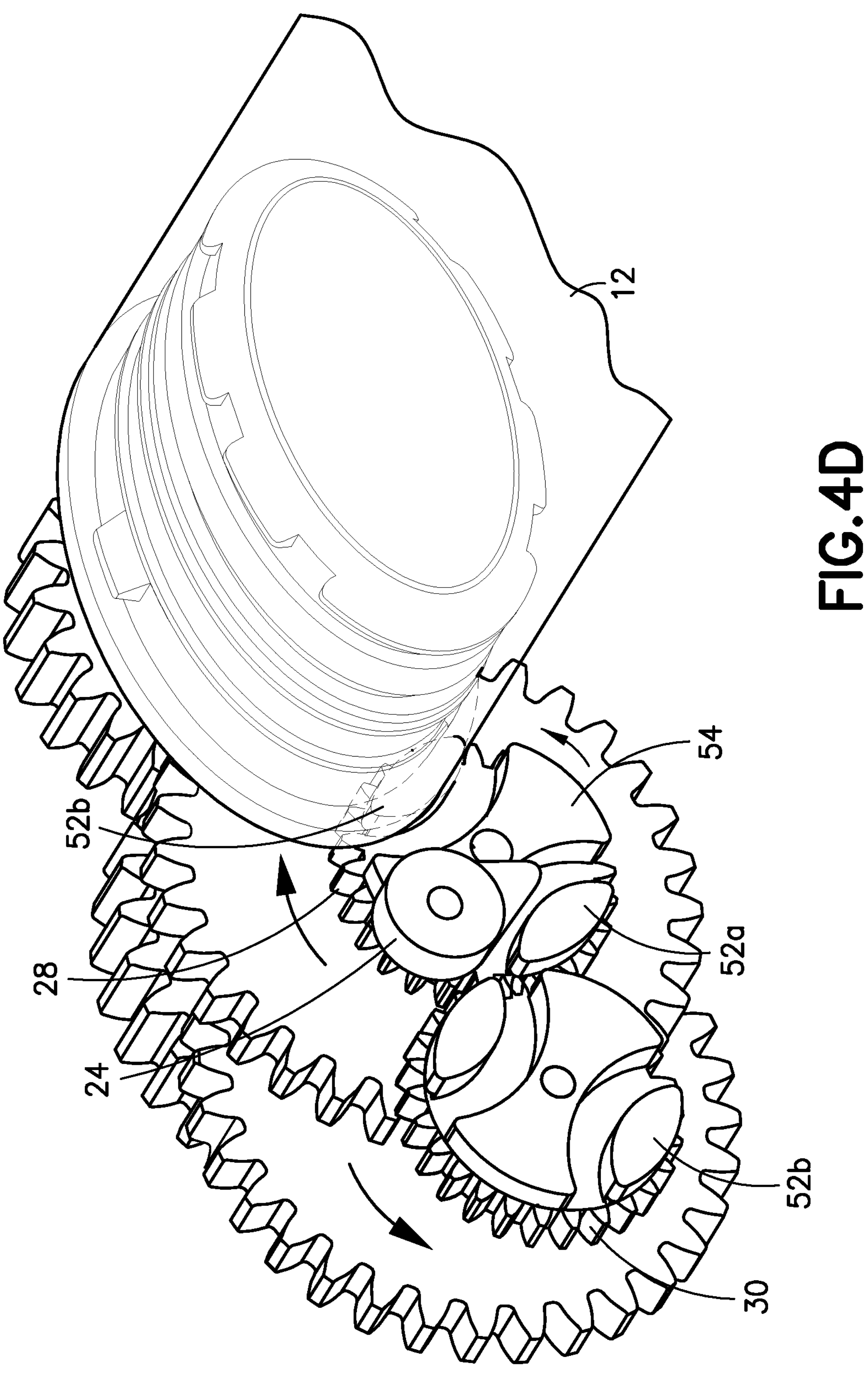
Figure 4E:
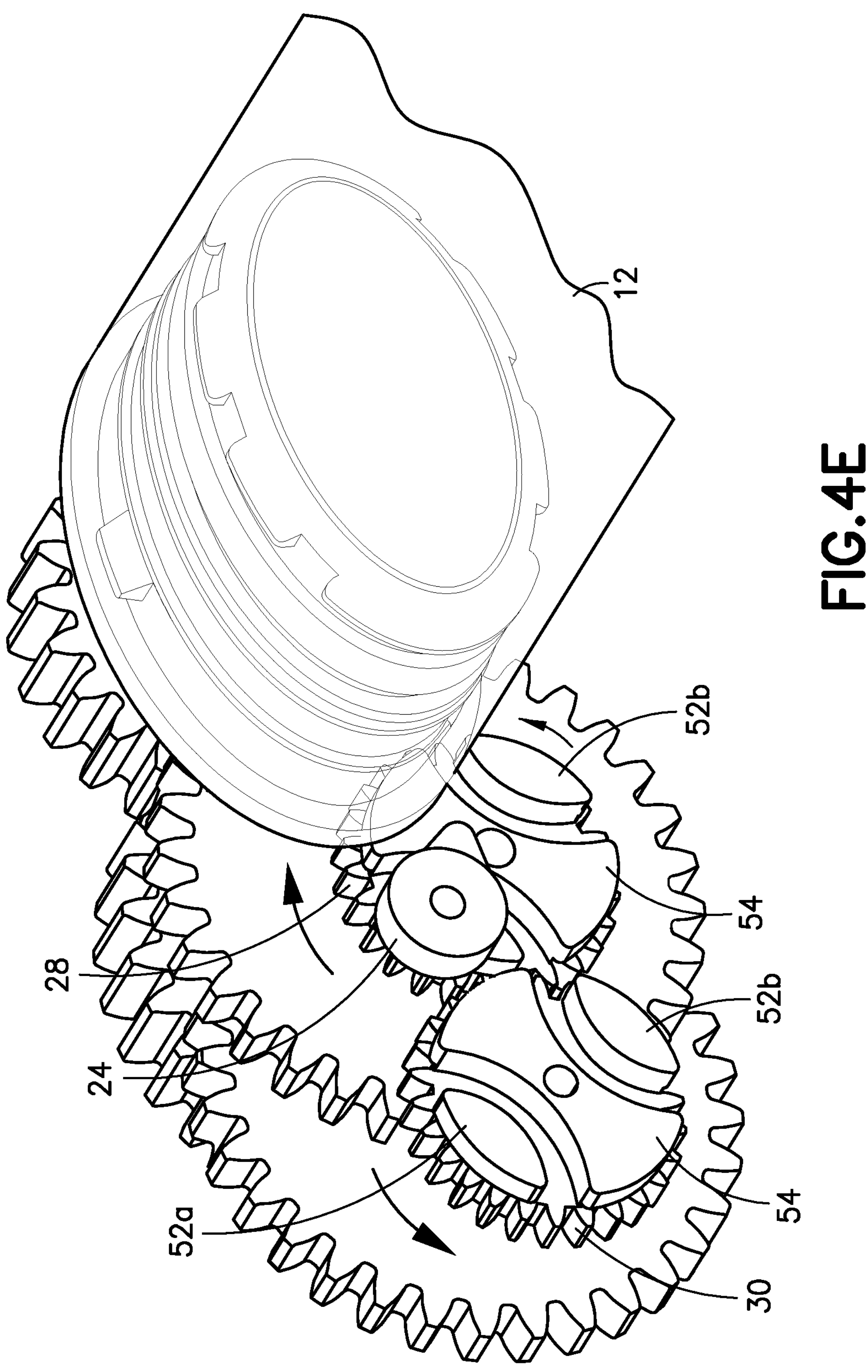
Figure 4F:
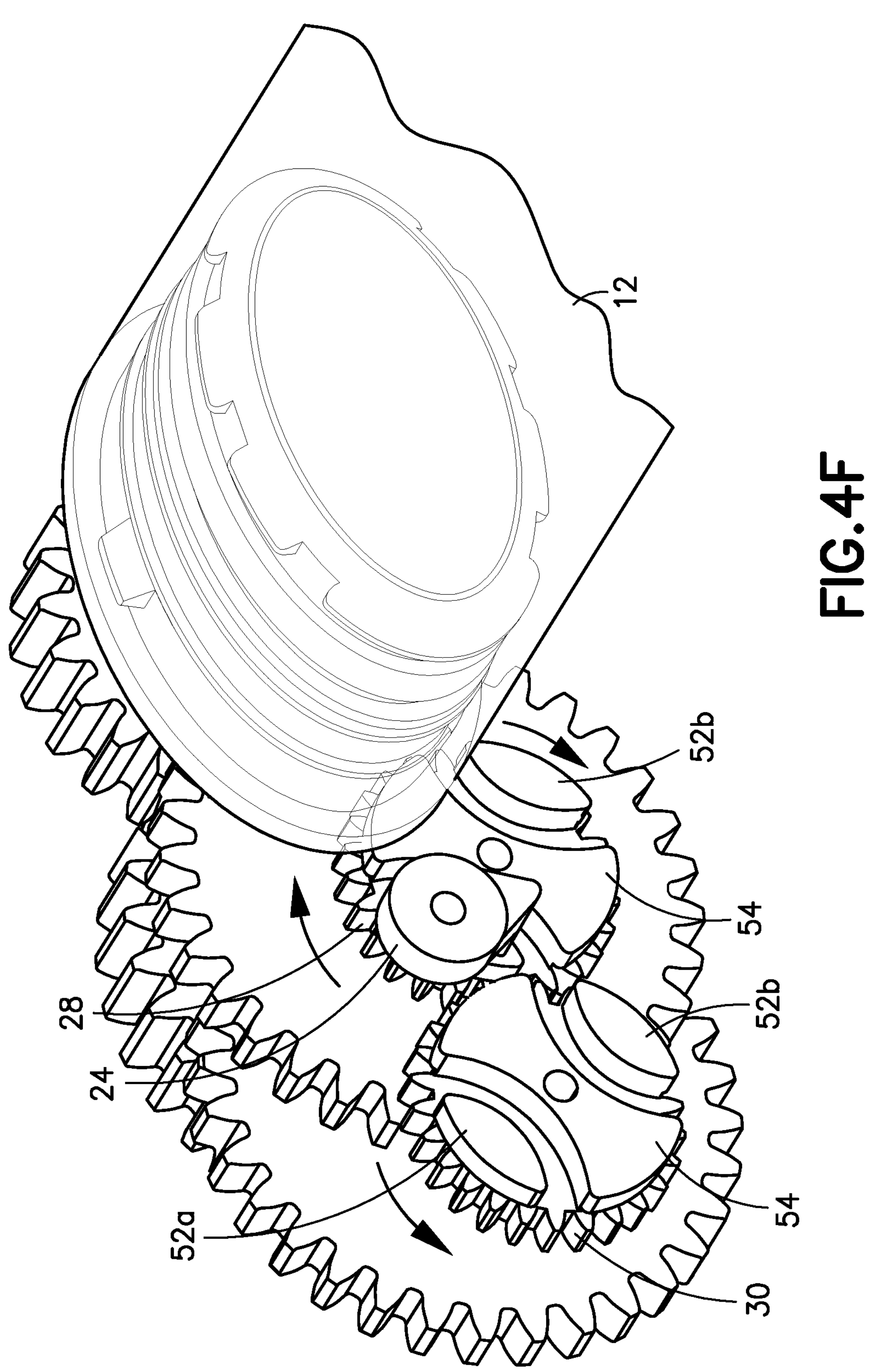

With reference to FIG. 4D, the pin 26 follows the lower concave surface of the concave lens-shaped protrusion 54 on spur gear 28, and moves the spur gear 28 CW 90 degrees as shown in FIG. 4E. The cooperating teeth on the spur gears 28 and 30 causes the spur gear 30 to rotate CCW 90 degrees. The cam surfaces of the double convex lens-shaped protrusion 52*a* and the double concave lens-shaped protrusion 54 on the spur gear 28 are configured to no longer push the pin 26 once it reaches at the other top end of the arc 32. Another S-shaped path 34 is established by respective grooves 50 on the spur gears 28, 30 for the CW movement of the pin 26 along the arc 32 as shown in FIG. 4F after the actuator 19 stops and reverses direction of the input shaft 20 connected to the plate 34. Either of the spur gears 28, 30 can be used as the output of the overrun prevention mechanism 22.

Another example embodiment of overrun prevention mechanism 22 will now be described with reference to FIGS. 5A through 5F. The front face 36 of each of the spur gears 28, 30 has two half-teardrop-shaped protrusions 70*a,b*. The plate 24 has two pins 26*a,b* and is shown connected to an input shaft 20 of the actuator. Spur gear 30 rotates CCW regardless of input direction of actuator input shaft 20. Spur gear 28 rotates CW regardless of input direction of actuator input shaft 20. The actuator input shaft 20 is rotated alternately CW and CCW to allow the pins 26 to travel through an arc 32 (e.g., 126 degrees or some other value less than 180 degrees) before stopping and reversing and traveling the arc in the opposite direction.

The half-teardrop-shaped protrusions 70*a,b* on each of the spur gears 28, 30 are arranged to be pushed by one of the corresponding pins 26*a,b* to turn that spur gear 28 or 30 by 90 degrees, causing the other spur gear to also turn by 90 degrees because of cooperating teeth therebetween. The half-teardrop-shaped protrusions 70*a,b* on a face of the spur gear 28 or 30 are arranged diagonally opposite each other with their flat surfaces facing each other. The pairs of half-teardrop-shaped protrusions 70*a,b* on the spur gears 28, 30 are offset with respect to each other, and the pins 26 *a,b* on the plate 24 are spaced with respect to each other such that the pin 26*b* pushes a flat surface of a half-teardrop-shaped protrusion 70 on the spur gear 30 as the plate 24 traverses CW at least part of the arc 32, and the pin 26*a* pushes a flat surface of a half-teardrop-shaped protrusion 70 on the spur gear 28 as the plate 24 traverses CCW at least part of the arc 32. In the example shown, the dimensions of the spur gears 28, 30 and their respective features 70*a,b* and the dimensions of the pins are configured to allow about 126 degrees of rotation of the input shaft 20 and plate 24 to cause about 90 degrees output from the spur gears 28, 30.

Figure 5A:
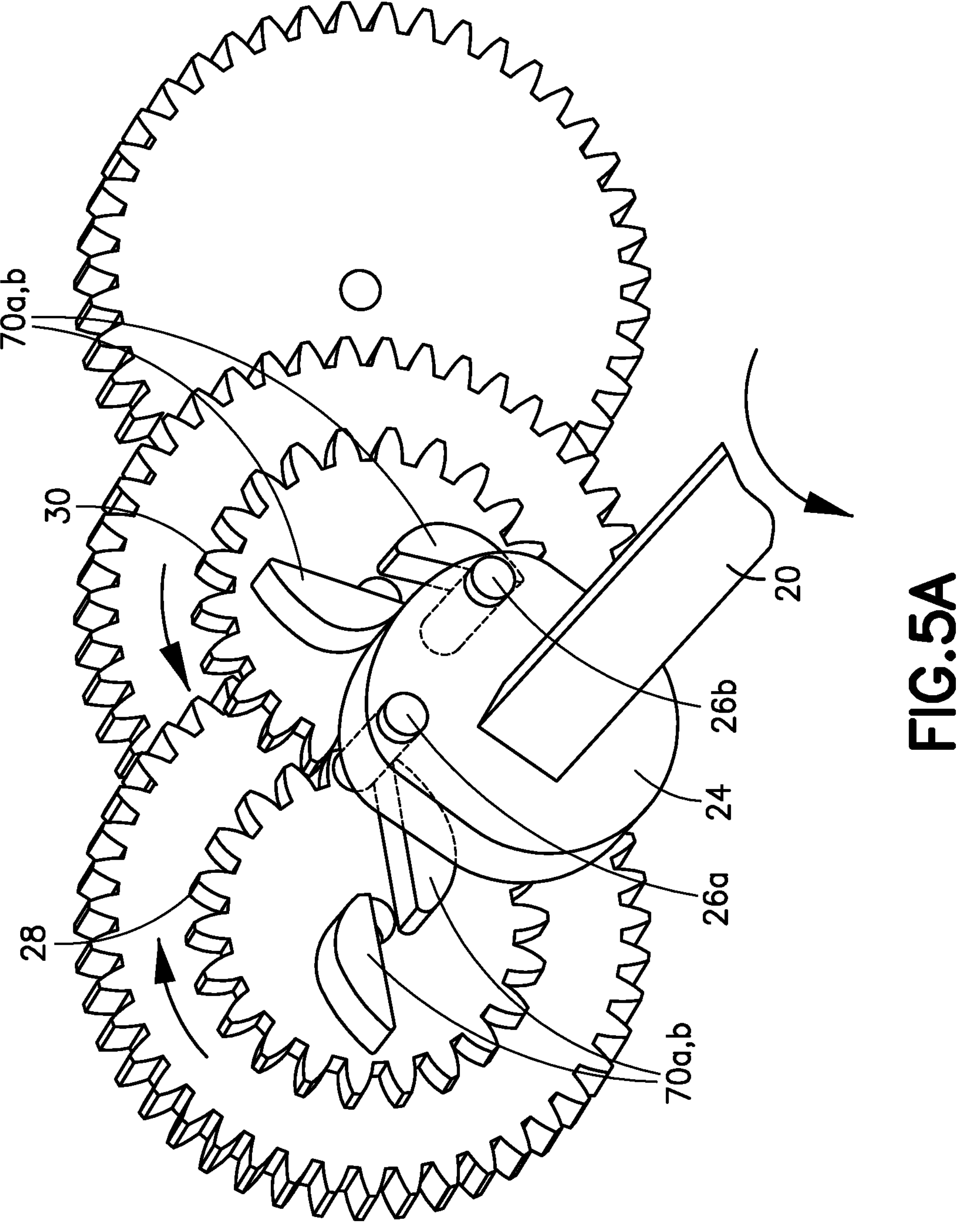
FIGS. 5A, 5B, 5C, 5D, 5E and 5F are side views of an actuator and gear train constructed in accordance with another illustrative embodiment for operating a drive mechanism of the example fluid delivery device of FIG. 1.
Figure 5B:
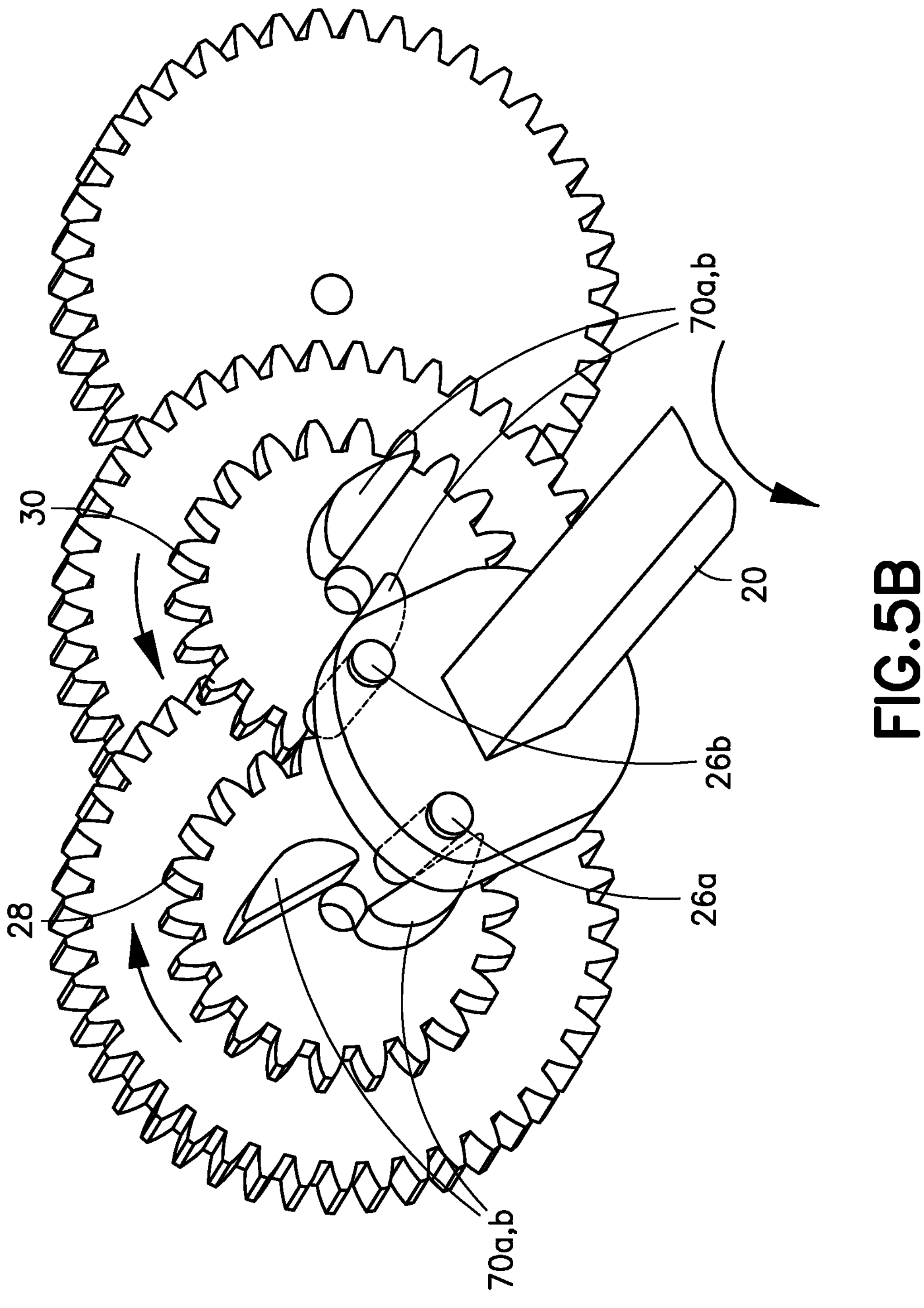
Figure 5C:
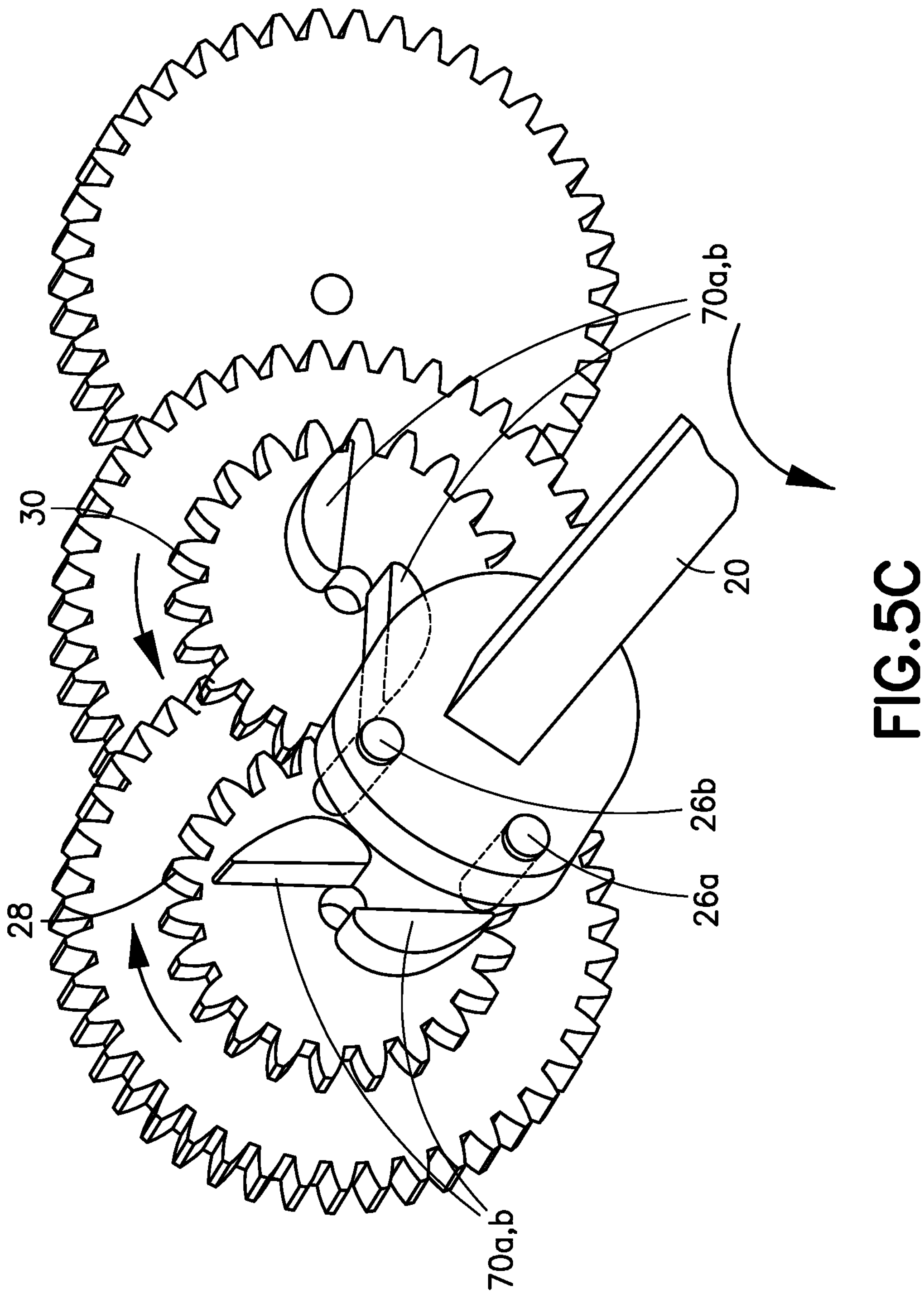
Figure 5D:
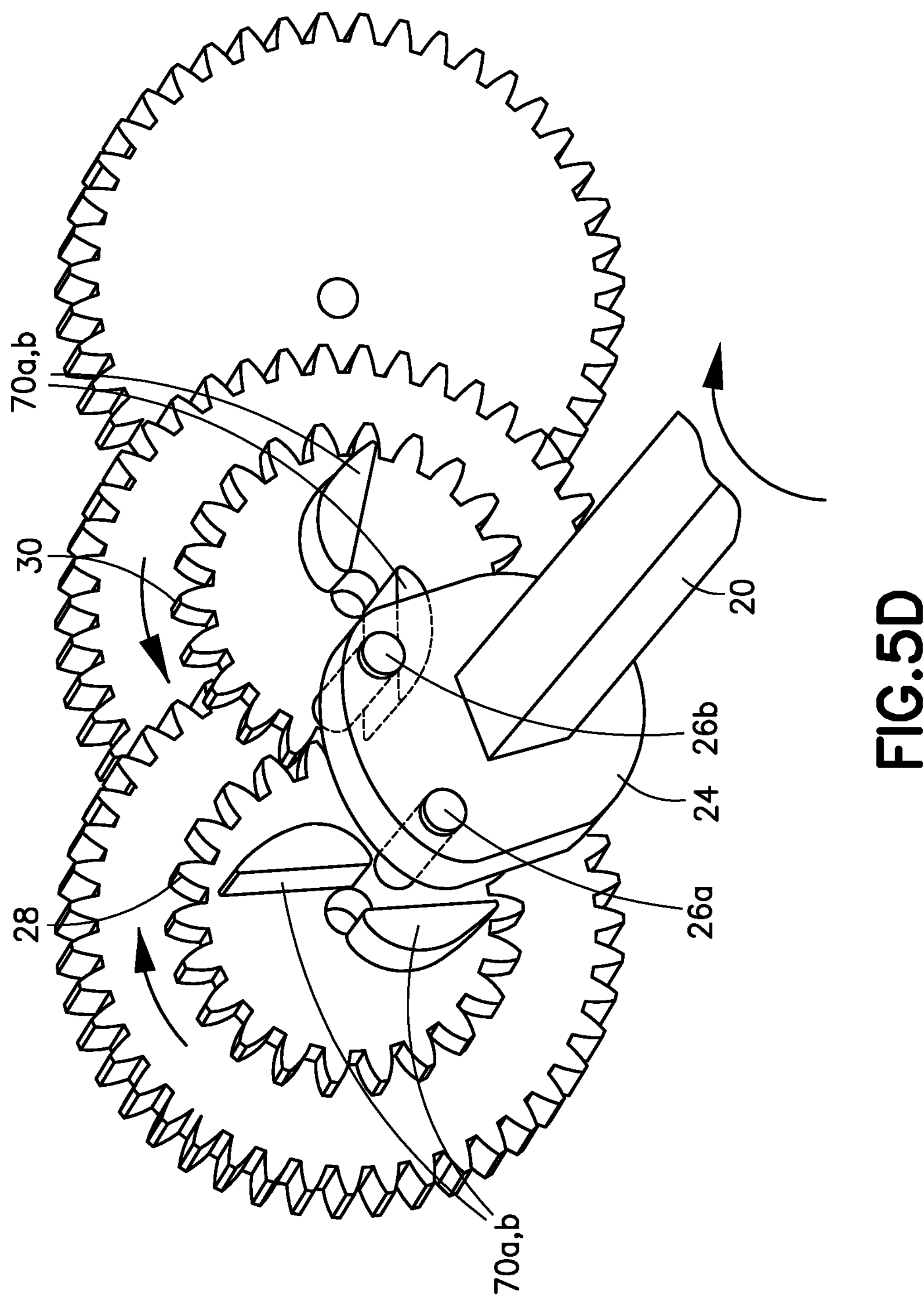
Figure 5E:
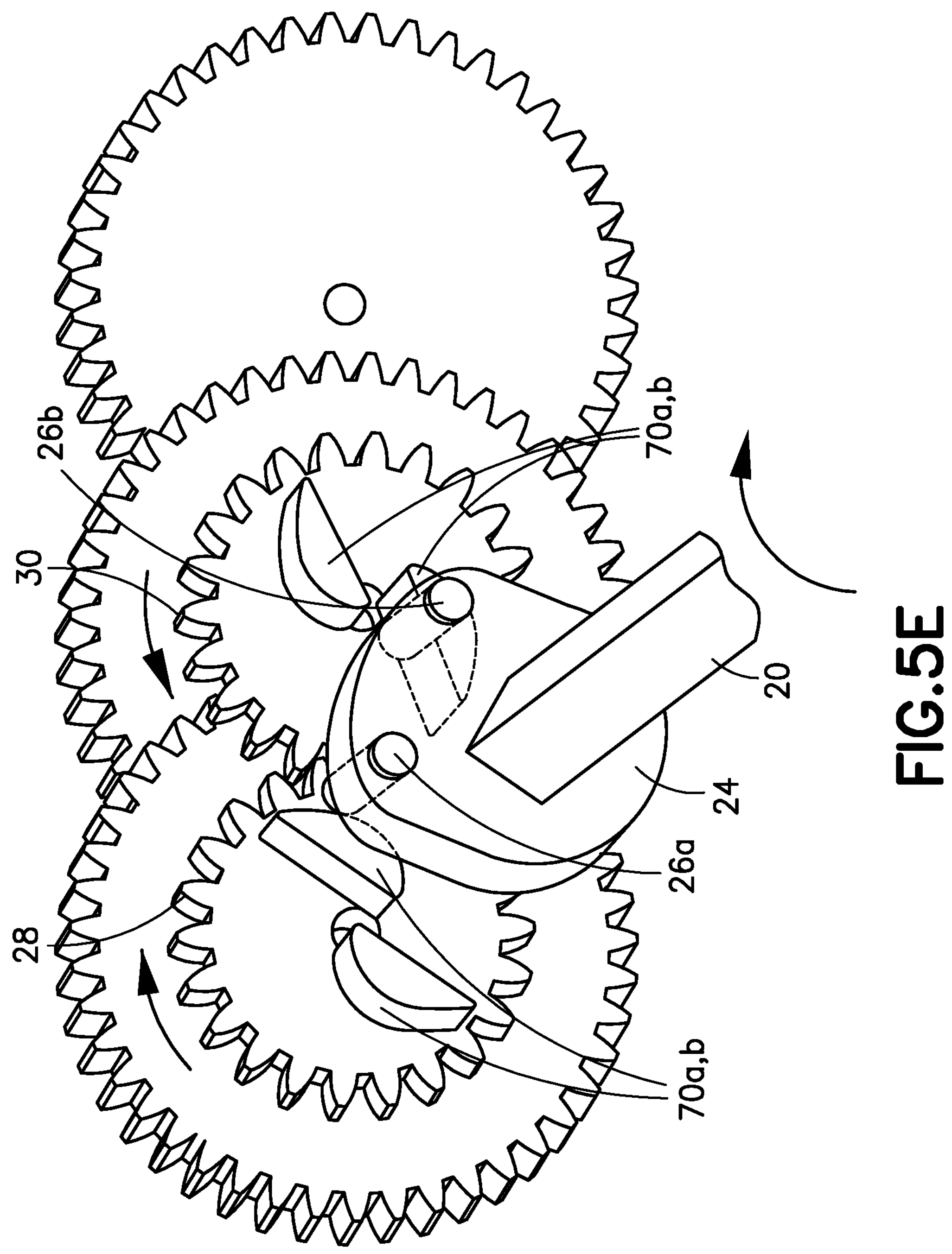
Figure 5F:
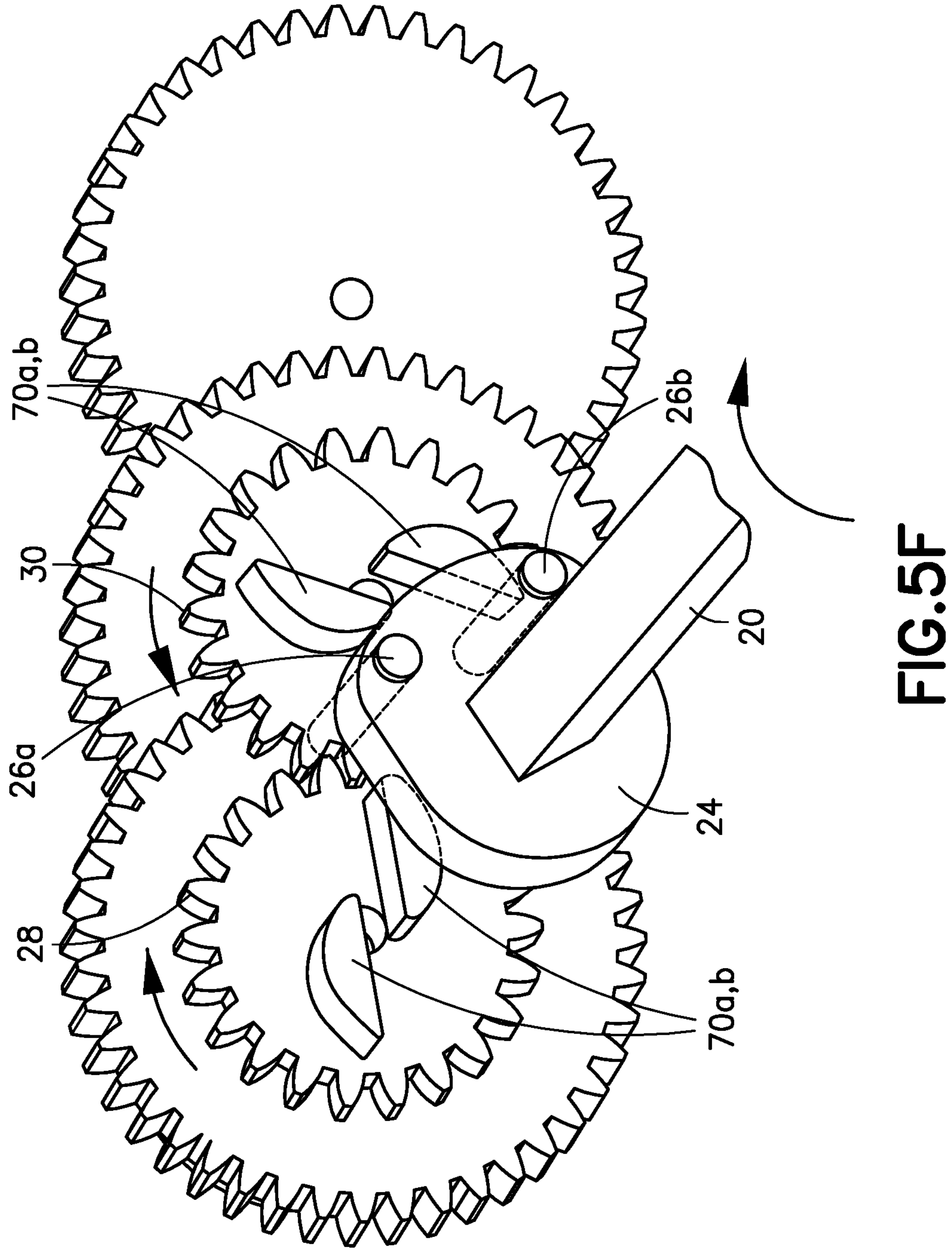

For example, FIG. 5A shows the input shaft 20 and plate 24 rotating CCW. The pin 26*a* travels along a flat surface of a half-teardrop-shaped protrusion 70 on the spur gear 28 to turn it 90 degrees CW. Spur gear 28 teeth, in turn, cooperate with teeth in the spur gear 30 to turn it 90 degrees CCW, as shown in FIGS. 5B and 5C. After the 90 degree rotation, the pin 26*a* is separated from the spur gear 28 and the spur gears stop rotating. The actuator then reverses direction and begins rotating the input shaft 20 and plate 24 CW as shown in FIG. 5D. Reversing the input rotational direction establishes contact between the other pin 26*b* and a half-teardrop-shaped protrusion 70 on the other spur gear 30. The pin 26*b* pushes the flat surface of the half-teardrop-shaped protrusion 70 as the plate 24 traverses the arc 32 CW to turn it 90 degrees CCW, as shown in FIGS. 5E and 5F. Spur gear 30 teeth, in turn, cooperate with teeth in the spur gear 28 to turn it 90 degrees CW. After the 90 degree rotation, the pin 26*b* is separated from the spur gear 30 and the spur gears stop rotating. The actuator then reverses direction and begins rotating the input shaft 20 and plate 24 CCW again. Either of the spur gears 28, 30 can be used as the output of the overrun prevention mechanism 22.

As stated above, the overrun prevention mechanism 22 described herein with regard to a technical solution and example embodiments can be implemented in a wearable infusion pump-type of fluid delivery device, and can also be used as the overdose prevention mechanism in medication delivery pens. The geometry of half-tear features 70 or protrusions 52, 54 on the faces of the spur gears 28, 30 can be modified for tuning the mechanism 22 input and output torque profiles. The pin(s) 26 illustrated herein can be replaced with pins with different cross section to achieve different load profile. The overrun prevention mechanism 22 can be fabricated in various sizes while maintaining its key features (e.g., half-tear features 70 or protrusions 52, 54), and be fabricated out of different materials. The spur gears 28 and 30 can be replaced with other gear types such as helical or bevel, while maintaining important features such as their CW and CCW rotations and cooperating teeth to turn the same amount after pin engagement to one of the spur gears' 28 and 30 features (e.g., half-tear features 70 or protrusions 52, 54). Also, the input rotation required for a full cycle and the output rotation can be modified to be other degrees besides 126 and 90 degrees respectively. The overrun prevention mechanism 22 can be modified for delivering different dose volumes based on the required specifications.

For reasons stated above, the overrun prevention mechanism 22 not only eliminates the risk of drug overdose, but also controls the accuracy of the delivered dose in each cycle. Also, due to the use of gears, the overrun prevention mechanism 22 operates at a similar noise level to rest of gear train components.

In addition, the overrun prevention mechanism 22 is advantageous because it can be located at different stages in the powertrain (e.g. before, after, or at the middle of gearbox). For example, spur gears are easily integrated with a gearbox often used for motors to impart motion to a drive mechanism for a plunger or piston in a fluid delivery device, and the overrun prevention mechanism 22 can be located at different stages of the powertrain (e.g. between the motor and gearbox, between the gearbox and pump mechanism, or internal to the gearbox). Moving overrun prevention mechanism 22 away from the pump (e.g., plunger 14 in syringe barrel 12) and closer to the actuator 19 has the added benefit of decreasing the torque values applied on it and reduces the risk of failure due to high loads.

The overrun prevention mechanism 22 has scalable gear ratio and can be configured to optimize the efficiency of the system based on the selection of other components such as actuator, gearbox, and pump mechanism. This technical solution is significantly more energy efficient than other indexing schemes such as the two ratchet wheel system of an Omnipod wearable pump developed by Insulet Corporation. Also, Omnipod works based on the complex interaction between multiple components (arms, shape memory alloy wires, ratchet wheels, hinge, stop pins, etc.) and small deviations in manufacturing or assembling process may result is failures in the device.

Although it can be combined with electronics for optimizing performance, the overrun prevention mechanism 22 is a purely mechanical solution and does not necessarily require electronics to operate, as opposed to a direct drive-type indexing system that requires electronics. Introducing electronics to the indexing system of a fluid delivery device may result in unwanted extra costs. As an example, a direct drive-type indexing system can require an encoder and possibly a secondary microprocessor to analyze the encoder data, which may dramatically increase the final cost of the fluid delivery device 10. By contrast, all components used in the overrun prevention mechanism 22 can be manufactured using inexpensive methods such as injection molding.

In addition, because of non-discreet output of a direct drive-type indexing system, errors occurring in the system for various reasons are cumulative and may add up to a higher error value during the lifetime of the fluid delivery device 10. On the other hand, each dose delivery cycle in the overrun prevention mechanism 22 is independent of previous cycles and errors are not transferred to the next dose delivery cycle.

As stated above, a conventional Geneva Mechanism does not have a feature to prevent the output from rotating in case of overrunning input. By contrast, the overrun prevention mechanism 22 prevents overdosing by stopping the output after reaching a certain condition. The overrun prevention mechanism 22 requires reversing the actuator 19 direction (e.g., motor direction) as a safety feature to continue the dosing process. On the other hand, a Geneva mechanism works continuously with a motor rotating in a single direction, which may cause overdosing the patient.

Example embodiments of the disclosure may address at least the above problems and/or disadvantages and other disadvantages not described above. Also, example embodiments are not required to overcome the disadvantages described above, and may not overcome any of the problems described above.

It will be understood by one skilled in the art that this disclosure is not limited in its application to the details of construction and the arrangement of components set forth in the above description or illustrated in the drawings. The embodiments herein are capable of other embodiments, and capable of being practiced or carried out in various ways. Also, it will be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings. Further, terms such as up, down, bottom, and top are relative, and are employed to aid illustration, but are not limiting.

The above-presented description and figures are intended by way of example only and are not intended to limit the illustrative embodiments in any way except as set forth in the following claims. It is particularly noted that persons skilled in the art can readily combine the various technical aspects of the various elements of the various illustrative embodiments that have been described above in numerous other ways, all of which are considered to be within the scope of the claims.

The invention claimed is:

1. A fluid delivery device comprising a drive mechanism with a rotary input to control fluid delivery components, an actuator to operate the drive mechanism, and an overrun prevention mechanism, the overrun prevention mechanism comprising:

first and second spur gears comprising gear teeth and disposed adjacent to each other, a selected number of the gear teeth of the first spur gear configured to engage a selected number of the gear teeth of the second spur gear which correspond to the selected number of the gear teeth of the first spur gear, the first spur gear rotatable clockwise and the second spur gear rotatable counterclockwise; and a plate with a pin configured to be actuated by the actuator in the fluid delivery device to rotate a controlled amount during a cycle among alternating cycles to move the pin in an arc path relative to the first and second spur gears, the plate configured to be actuated to rotate in clockwise and counterclockwise directions in the alternating cycles;

wherein the first and second spur gears each have a face directed toward the plate with the pin, each face being configured with at least one surface feature along which the pin can follow as the plate is rotating, the at least one surface feature of each of the first and second spur gears configured to be contacted by the pin when traveling toward respective ends of the arc path to rotate the corresponding one of the first and second spur gears by a selected amount and teeth of the corresponding one of the first and second spur gears engaging teeth of the other one of the first and second spur gears to impart rotation, the at least one surface feature of each of the first and second spur gears is also configured to disengage with the pin at each of the respective ends of the arc path before the actuator reverses a direction of rotation of the plate to commence another cycle among the alternating cycles.

2. The fluid delivery device of claim 1, wherein an input to the overrun prevention mechanism corresponds to 126 degrees of rotation of the plate along the arc path during a respective one of the alternating cycles, and the first and second spur gears are configured to rotate 90 degrees during the respective one of the alternating cycles.

3. The fluid delivery device of claim 2, wherein an output of the overrun prevention mechanism is a 90 degree rotation imparted by one of the first and second spur gears being rotated 90 degrees during a respective one of the alternating cycles.

4. The fluid delivery device of claim 3, wherein the fluid delivery device has gear train components configured to receive the output of the overrun prevention mechanism as an input and to generate a second output of smaller rotation for application to the drive mechanism to achieve a fluid dose of a predetermined amount.

5. The fluid delivery device of claim 4, wherein the fluid delivery device is a syringe-type pump configured to move a plunger in a barrel-type reservoir and the drive mechanism comprises telescopic nested screws operable to move the plunger, the second output configured to be provided to the drive mechanism to move the plunger a distance commensurate to deliver the fluid dose of the predetermined amount.

6. The fluid delivery device of claim 1, wherein the at least one surface feature of each face comprises two arcuate grooves that define two double convex lens-shaped protrusions disposed on either side of a center double concave lens-shaped protrusion.

7. The fluid delivery device of claim 6, wherein a convex surface on the double concave lens-shaped protrusion is configured to be contacted by the pin when traveling toward one of the respective ends of the arc path to rotate the corresponding one of the first and second spur gears by a selected amount.

8. The fluid delivery device of claim 6, wherein the two double convex lens-shaped protrusions and the center double concave lens-shaped protrusion are configured to disengage the pin to not rotate further once the pin has reached one of the respective ends of the arc path.

9. The fluid delivery device of claim 1, wherein the at least one surface feature of each face comprises half-teardrop-shaped protrusions, each of the half-teardrop-shaped protrusions having a flat surface and a convex surface.

10. The fluid delivery device of claim 9, wherein the half-teardrop-shaped protrusions are arranged diagonally opposite each other on the face of each of the first and second spur gears with the flat surface of each of the half-teardrop-shaped protrusions facing each other.

11. The fluid delivery device of claim 1, further comprising a sensor for detecting when the pin reaches one of the respective ends of the arc path.

12. The fluid delivery device of claim 11, wherein the fluid delivery device is configured to have a processor to receive outputs of the sensor and to control the actuator to reverse a direction when the outputs indicate one of the respective ends of the arc path has been reached by the pin.

* * * * *